United States Patent [19]

Chasar

[11] 4,032,505

[45] June 28, 1977

[54] 2,4-DIHYDROXYDIPHENYL SULFOXIDE

[75] Inventor: Dwight William Chasar, Northfield, Ohio

[73] Assignee: The B. F. Goodrich Company, Akron, Ohio

[22] Filed: Nov. 2, 1976

[21] Appl. No.: 737,955

[52] U.S. Cl. .................. 260/45.8 N; 260/45.95 C; 260/607 AR
[51] Int. Cl.² .................... C08K 5/41; C07C 39/12
[58] Field of Search ............ 260/45.95 C, 607 AR, 260/45.8 N

[56]     References Cited
       UNITED STATES PATENTS

| 2,288,282 | 6/1942 | Huismann | 260/607 AR |
| 2,560,049 | 7/1951 | Cook | 260/607 AR |
| 2,661,376 | 12/1953 | Comer et al. | 260/607 AR |
| 3,649,695 | 3/1972 | Millionis | 260/45.95 C |
| 3,857,896 | 12/1974 | Desjariais | 260/607 AR |

FOREIGN PATENTS OR APPLICATIONS 554,581  3/1958  Canada ................... 260/607 A Primary Examiner—V. P. Hoke
Attorney, Agent, or Firm—J. Hughes Powell, Jr.

[57]    ABSTRACT 2,4-Dihydroxydiphenyl sulfoxide prepared by the reaction of benzenesulfinyl chloride and resorcinol is useful as a photostabilizer for polyolefins.

8 Claims, No Drawings

2,4-DIHYDROXYDIPHENYL SULFOXIDE

BACKGROUND OF THE INVENTION

Symmetrical hydroxydiaryl sulfoxides are known and can be prepared by the following reaction.

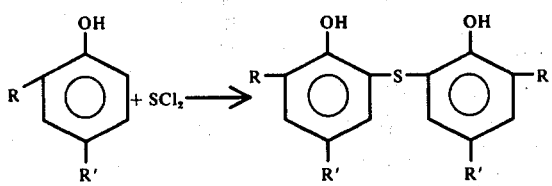

These compounds are then oxidized to the corresponding sulfoxides. The unsymmetrical hydroxydiaryl sulfoxides are not prepared by this reaction, but normally require four or more low yield consecutive reactions. Some of the symmetrical hydroxydiaryl compounds such as 4,4'thiobis(resorcinol) have been used to stabilize pine rosin.

SUMMARY OF THE INVENTION 2,4-Dihydroxydiphenyl sulfoxide is readily prepared by a reaction of benzenesulfinyl chloride and resorcinol and quite unexpectedly has been found to be a satisfactory photostabilizer for polyolefins.

DETAILED DESCRIPTION

In the reaction of benzenesulfinyl chloride with resorcinol, about 1 mol of the benzenesulfinyl chloride and about one mol of resorcinol are reacted with at least an equimolar amount of aluminum chloride in a polar solvent at a temperature below 50° C., preferably below about 25° C. If the temperature is conducted at too low a temperature, the reaction is too slow to be practical, and more preferably is greater than about 0° C. While molar excess of reactants may be used, there is no real advantage, and less than molar amounts of a reactant will result in lower yields. A useful solvent is dichloromethane and other solvents including chloroform, benzene, trichloroethane, ethylene dichloride, and the like may be used as solvents. An advantage of this one step reaction is that total yields greater than about 50% can be obtained.

2,4-Dihydroxydiphenyl sulfoxide in amounts as low as 0.01, more preferably about 0.1 to as high as 5 to 10 weight parts per 100 weight parts, of polymer provide increased resistance to light induced degradation in polyolefins.

Polyolefins having molecular weights of at least about 2,000 which may be photostabilized in accordance with this invention include homopolymers of α-olefins including those of ethylene, propylene, butene-1, isobutylene, pentene-1, hexene-1, 4-methyl-1-pentene, and the like; copolymers thereof such as ethylene, propylene, ethylene butene-1, 4-methyl-1-pentene, hexene-1, and the like; ethylene α-olefin diene rubbers wherein the α-olefin is preferably propylene or butene-1 and the diene is 1,4-hexadiene, 2-methyl-1,4-hexadiene, dimethyl-1,4,9-decatriene, dicyclopentadiene, vinyl cyclohexane, vinyl norbornene, 2-ethylidene norbornene, norbornadiene, methyl tetrahydroindene, and the like as is well known.

The 2,4-dihydroxydiphenyl sulfoxide is readily incorporated into the polyolefin by conventional methods including powder mixing, milling or banbury mixing, extruding and the like, as such; in a solvent or masterbatched. Conventional compounding ingredients will also be used in conjunction with the sulfoxide; including fillers, reinforcing agents, processing oils, plasticizers, lubricants, curing agents, antioxidants, antiozonants, color and heat stabilizers, other ultraviolet absorbers, and the like.

This sulfoxide has been found to be particularly useful when used in conjunction with other stabilizers, particularly aromatic hydroxy stabilizers, and more particularly, unexpected synergistic activity is obtained with certain hydroxyphenyl alkeneyl isocyanurates of the formula

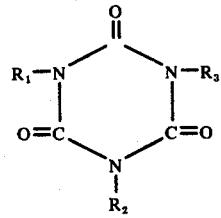

wherein $R_3$ is a hydroxyphenylalkyleneyl radical having the formula

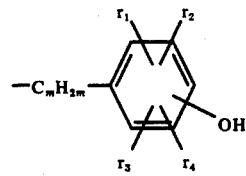

wherein $m$ is an integer from 1 to 4, $r_1$ is an alkyl group positioned immediately adjacent to the hydroxyl group on the ring and contains from 1 to 18 carbon atoms and $r_2$, $r_3$ and $r_4$ are selected from the group consisting of hydrogen or an alkyl group containing from 1 to 18 carbon atoms; and $R_1$ and $R_2$ are selected from the group consisting of hydrogen or R. The amounts of the combination used will be from about 0.5 total to about 10 weight parts per 100 weight parts of polymer in a value of about 1:10 to 10:1 of each.

EXAMPLE I 2,4-Dihydroxydiphenyl sulfoxide is pepared by slowly adding benzenesulfinyl chloride (40.15 grams, 0.25 mol) to an agitated suspension of resorcinol (27.53 grams, 0.25 mol) and anhydrous aluminum chloride (33.38 grams, 0.25 mol) in 400 ml of methylene chloride at 0° under nitrogen. The mixture was stirred at 0° for 3 hours. 300 ml of water was then added and a pink solid was isolated from the mixture. The methylene chloride layer was separated from the water layer and the solid dissolved in 300 ml acetone and this solution combined with the methylene chloride layer and the resulting solution was dried over anhydrous magnesium sulfate, filtered and the solvents evaporated to afford a viscous pink oil. The residual oil was refluxed in 600 ml of chloroform for 6 to 8 hours, the hot solution filtered and allowed to cool. 40 grams of 2,4-dihydroxydiphenyl sulfoxide was obtained for a total yield of 69%. The melting point was 129°–130° C. Infrared spectra confirmed the presence of OH and S=O groups. NMR spectra demonstrated the presence of hydroxyl groups at the 2 and 4 positions, hydrogen at the 3 and 5 positions and at the 2', 3', 4', 5', 6' and 6 positions. The UV spectra was also determined.

EXAMPLE II

The 2,4-dihydroxydiphenyl sulfoxide prepared in accordance with Example I was blended with polypropylene in the amounts set forth in the table below and the blend extruded. The extrudate was pressed into 10 ml thick sheets which were cut into 1 × 2 inch sample plaques. The sample plaques were mounted on holders of the size to fit an infrared spectrometer and placed in a Weatherometer. At various time intervals the samples were removed and their infrared spectra from 1910 to 1700 $cm^{-1}$ are recorded. The development of carbonyl at 1720 $cm^{-1}$ relative to the reference peak at 1890 $cm^{-1}$ (carbonyl index) against time is monitored. The time for the carbonyl index to reach 40 is the failure time. Samples were also tested for antioxidant screening by mounting sample plaques on a glass rod which are placed in a draft oven at 140° C. The failure time is that taken as time when any portion of the plaque becomes brittle.

| 2,4-dihydroxy-diphenyl sulfoxide weight/parts | 140 C. oven aging days | Weatherometer hours |
|---|---|---|
| 0 | ½ | 200 |
| 0.1 | 1-3 | — |
| 0.5 | 7 | 1475 |

The above results are to be compared to a symmetrical dihydroxy sulfide in 10 ml polypropylene. For example, bis(2-hydroxy-3-butyl-5-methylphenyl) sulfide at a 0.5 weight part level at 140° C. oven aging for 1-3 days and only 396 hours in the weatherometer. 0.1 weight part of bis(4-hydroxy-3-butyl-5-methylphenyl) sulfide showed 1-3 days oven aging at 140° C. for 490 hours in the weatherometer.

To demonstrate an important synergistic advantage of using small amounts of other stabilizers with the 2,4-dihydroxydiphenyl sulfoxide, 0.25 weight part of tris(3,5-di-t-butyl-4-hydroxyphenyl)isocyanurate was mixed into a composition containing 0.5 weight part of the sulfoxide. When tested for oven aging, this sample containing both materials was heat stable for 44 days as compared to 7 days for the sulfoxide alone, and 31 days for the isocyanurate alone. The combination demonstrated resistance to light by lasting about 813 hours in the weatherometer.

I claim:
1. 2,4-Dihydroxydiphenyl sulfoxide.
2. A composition comprising a polyolefin and a stabilizing amount of 2,4-dihydroxydiphenyl sulfoxide.
3. The composition of claim 2 wherein the polyolefin is polypropylene and said sulfoxide is present in amount of about 0.1 to 10 weight part per 100 weight part of polypropylene.
4. The composition of claim 2 containing at least one other aromatic hydroxy stabilizer.
5. The composition of claim 4 wherein said other stabilizer is a hydroxyphenyl alkenyl isocyanurate.
6. The composition of claim 5 wherein said isocyanurate is tris(3,5-di-t-butyl-4-hydroxyphenyl)isocyanurate present in amount of about 0.1 to about 5 weight parts per 100 weight of polyolefin.
7. A method for preparing 2,4-dihydroxydiphenyl sulfoxide by reacting together benzenesulfinyl chloride and resorcinol in the presence of aluminum chloride.
8. The process of claim 7 wherein there is used about an equimolar amount of each of said reactants.

* * * * *